United States Patent
Kim

(10) Patent No.: US 8,382,712 B2
(45) Date of Patent: Feb. 26, 2013

(54) FILTER DEVICE AND LIQUID INJECTION APPARATUS HAVING THE SAME

(75) Inventor: Yong-Nyun Kim, Goyang-si (KR)

(73) Assignee: E-Wha Fresenius Kabi Inc., Gunpo-Si, Gyeonggi-Do (KR)

( * ) Notice: Subject to any disclaimer, the term of this patent is extended or adjusted under 35 U.S.C. 154(b) by 22 days.

(21) Appl. No.: 13/148,358

(22) PCT Filed: Feb. 10, 2010

(86) PCT No.: PCT/KR2010/000578
§ 371 (c)(1),
(2), (4) Date: Aug. 8, 2011

(87) PCT Pub. No.: WO2010/090418
PCT Pub. Date: Aug. 12, 2010

(65) Prior Publication Data
US 2012/0022449 A1     Jan. 26, 2012

(30) Foreign Application Priority Data

Feb. 9, 2009 (KR) .................. 10-2009-0010336
Dec. 31, 2009 (KR) .................. 10-2009-0136275

(51) Int. Cl.
*A61M 1/00* (2006.01)
(52) U.S. Cl. ..................... 604/126; 604/122
(58) Field of Classification Search .......... 604/122, 604/126
See application file for complete search history.

(56) References Cited

U.S. PATENT DOCUMENTS

| | | | |
|---|---|---|---|
| 3,943,056 A | 3/1976 | Hultsch et al. | |
| 4,642,098 A * | 2/1987 | Lundquist | 604/123 |
| 4,900,308 A * | 2/1990 | Verkaart | 604/126 |
| 5,472,605 A | 12/1995 | Zuk, Jr. | |
| 6,913,590 B2 * | 7/2005 | Sorenson et al. | 604/29 |
| 2002/0123715 A1 * | 9/2002 | Sorenson et al. | 604/29 |
| 2004/0188344 A1 | 9/2004 | Scott et al. | |
| 2005/0131340 A1 * | 6/2005 | Sorenson et al. | 604/29 |

\* cited by examiner

FOREIGN PATENT DOCUMENTS

| | | |
|---|---|---|
| EP | 1803471 A1 | 7/2007 |
| WO | 97-42410 A1 | 11/1997 |

OTHER PUBLICATIONS

International Search Report for PCT/KR2010/000578 mailed on Oct. 11, 2010.

*Primary Examiner* — Victoria P Shumate
(74) *Attorney, Agent, or Firm* — Lucas & Mercanti, LLP

(57) ABSTRACT

A filter device of the present invention includes a hydrophilic filter located in a vertical space in a filter housing to filter off solid impurities in an introduced liquid, at least one hydrophobic filter located corresponding to at least one gas discharge hole provided in the filter housing, the hydrophobic filter allowing gas in the introduced liquid to be discharged to the outside before and/or after the liquid passes through the hydrophilic filter, and a blocking member for preventing gas in the liquid passing through the hydrophilic filter from flowing into the outlet tube, the blocking member being installed in the filter housing to block the outlet tube, the blocking member having a longitudinal passage formed in a center portion thereof so that the liquid is introduced into the outlet tube through the passage and discharged therefrom. According to the present invention, there are advantages in that the filter device can effectively remove air and impurities such as solid particles contained in a liquid such as a medicine, prevent the air in the medicine from flowing into an extension tube connected to the filter device, and ensure a maximum surface area of a hydrophilic filter for filtering off solid particles such as glass fragments so that a flow rate of a medicine passing through the filter device does not decrease.

18 Claims, 13 Drawing Sheets

Fig. 5
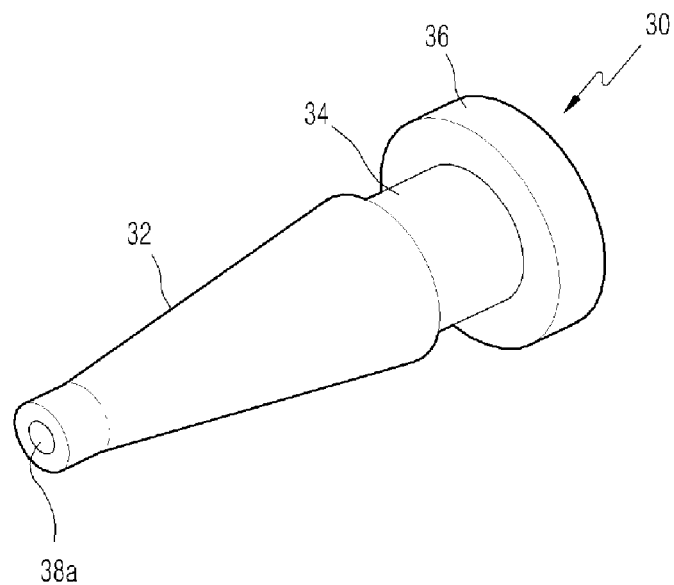
(a)
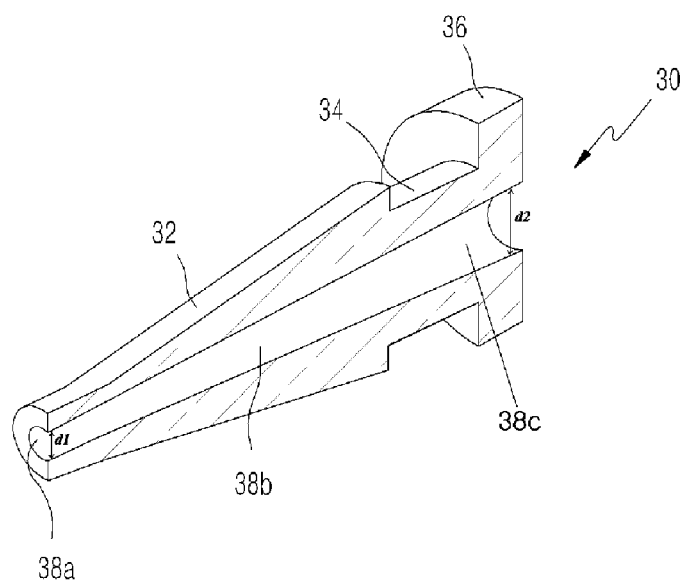
(b)

Fig. 6
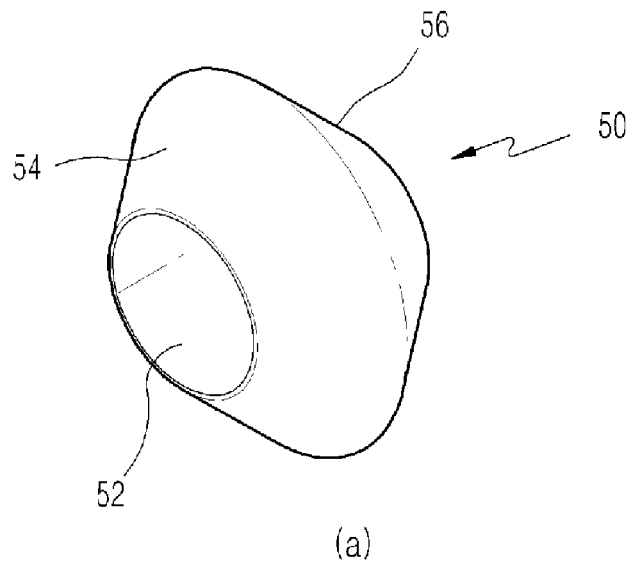
(a)
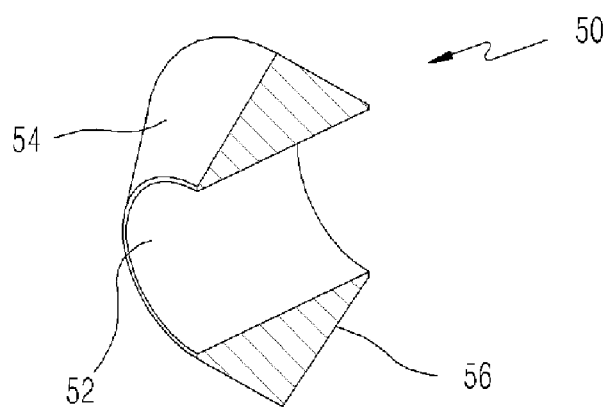
(b)

FILTER DEVICE AND LIQUID INJECTION APPARATUS HAVING THE SAME

CROSS-REFERENCE TO RELATED APPLICATIONS

This application is a 371 of PCT/KR2010/000578 filed on Feb. 1, 2010, which claims the benefit of Korean Patent Application Nos. 10-2009-0010336 filed on Feb. 9, 2009, and 10-2009-0136275 filed on Dec. 31, 2009, the contents of each of which are incorporated herein by reference.

TECHNICAL FIELD

The present invention relates to a filter device, and more particularly, to a filter device which effectively removes air and impurities such as solid particles contained in a liquid such as a medicine, prevents the air in the medicine from flowing into an extension tube connected to the filter device, and ensures a maximum surface area of a hydrophilic filter for filtering off solid particles such as glass fragments so that a flow rate of a medicine passing through the filter device does not decrease.

In addition, the present invention relates to a filter device which can prevent impurities of adhesive components from flowing into the filter device and/or a capillary tube when the capillary tube in the extension tube is sealably connected to the filter device by an adhesive using a conventional method.

Further, the present invention relates to a liquid injection apparatus including such a filter device.

BACKGROUND ART

Generally, in many occasions, an injectable liquid should be continuously injected to a patient. At this time, a liquid injection apparatus is used, and the liquid injection apparatus includes a filter device for removing impurities and air contained in the injectable liquid.

FIG. 12 is a perspective view showing an example of a conventional liquid injection apparatus, which may be referred to in U.S. Pat. No. 4,781,698.

A liquid injection apparatus 1000 includes an injectable liquid storing means 102 such as a bottle or pack where an injectable liquid is stored, and a flexible extension tube 104 extending from the injectable liquid storing means 102 to transport the injectable liquid supplied from the injectable liquid storing means 102. A dropping unit 106 partially inserted into the injectable liquid storing means 102 to drop the injectable liquid is integrally provided at an upstream end of the extension tube 104, and a control means 108 for controlling the amount of the supplied injectable liquid by blocking the flow of the injectable liquid flowing along the extension tube 104 is provided in the middle portion of the extension tube 104. In addition, there is provided a filter device 100 for filtering the supplied injectable liquid to remove impurities and air in the supplied injectable liquid, and a distal end connector 110 to which an injection needle N inserted into the body of a patient is detachably coupled is provided at the rear end of the corresponding extension tube 104.

Here, the extension tube 104 is provided to have the same inner diameter over the entire moving path of the injectable liquid, and instead of the injection needle N, a catheter well known in the art may also be coupled to the distal end connector 110 of the extension tube 104. A cap (not shown) is coupled to the distal end connector 110 so as to prevent the injectable liquid from being contaminated before the liquid injection apparatus 1000 is used. To use the liquid injection apparatus 1000, the corresponding cap is removed and wasted from the distal end connector, and the injection needle N or catheter is coupled thereto.

In addition, if a user (a nurse or the like) inserts the injection needle N into the body of a patient and then completely controls the amount of injected liquid by using the control means 108, the injectable liquid stored in the injectable liquid storing means 102 is discharged and supplied by small quantity, flows along the extension tube 104, and then, is injected into the body of the patient through the injection needle N coupled to the distal end connector 110.

Meanwhile, if impurities (for example, glass fragments generated in opening a glass ampoule) or air is injected together with an injectable liquid into the body of a patient, such impurities or air may damage the blood vessel or brain of the patient and cause a fatal danger. Therefore, in order to prevent this problem, the filter device 100 described above is provided on the path of the extension tube 104, and the capillary tube is provided in a distal end of the extension tube 104 connected to the filter device 100. The capillary tube installed in the distal end of the extension tube 104 prevents the medicine causing a fatal damage to the organ of the patent when injected fast, such as an anticancer medicine or antibiotics, from being excessively injected.

An example of the filter device 100 of the above liquid injection apparatus 1000 is shown in FIG. 13. Referring to the sectional view of FIG. 13, the filter device 100 includes filter receiving plates 100a-1 and 100a-2 made of synthetic resin provided at an outer side thereof to be spaced apart from each other in parallel to define a predetermined space therein, and both ends of the filter receiving plates 100a-1 and 100a-2 are converged and connected to the extension tube 104 so that the internal space communicates with the extension tube.

Two thin sheet-type filters 100b-1 and 100b-2 in parallel with each other are housed in the internal space defined by both the filter receiving plates 100a-1 and 100a-2. The liquid permeable filter 100b-1 is provided at the side where an injectable liquid flows in, and the gas permeable filter 100b-2 is provided at the next, wherein the filters 100b-1 and 100b-2 are made of porous synthetic resin material with a predetermined mesh. In addition, in the filter receiving plate 100a-2 in which the gas permeable filter 100b-2 is provided, an air discharge hole 100a-2-1 is formed at a corresponding location.

Therefore, in the conventional filter device 100 as shown in FIG. 13, if the injectable liquid supplied from the injectable liquid storing means 102 flows into the filter device 100, impurities such as glass fragments contained in the corresponding injectable liquid are filtered off while the injectable liquid passes through the liquid permeable filter 100b-1, and then, if the corresponding injectable liquid passes through the gas permeable filter 100b-2, the air is discharged to the outside through the air discharge hole 100a-2-1 after the injectable liquid passes through the gas permeable filter 100b-2. However, the conventional filter device has a problem in that a flow rate of the injectable liquid is lowered since two filters 100b-1 and 100b-2 blocks the flow path of the injectable liquid. In addition, the conventional filter device has a structural limit in that the air in the injectable liquid is not entirely discharged through the air discharge hole 100a-2-1 after passing through the gas permeable filter 100b-2, but partially flows into the extension tube 104. Moreover, the capillary tube installed in the distal end of the extension tube 104 should be sealably connected to the filter device 100, and at this time impurities of adhesive components flow into the filter device and/or the capillary tube.

In order to overcome the above problems, the present inventors have suggested new filter devices and a liquid injection apparatus having the same. These new devices are configured to effectively remove air or solid impurities such as glass fragments in the medicine. Examples of such new devices are disclosed in Korean Patent Application Nos. 10-2006-0033027 and 10-2007-0051334. These filter devices are excellent, but they can be improved further in common with other excellent technologies.

Particularly, in the technical field of the present invention, there are unceasing demands on the improvement of a filter device capable of effectively removing air and solid impurities such as glass fragments in a medicine and allowing sealable connection with a capillary in the extension tube without adhesive while minimizing a change in flow rate of the medicine.

SUMMARY OF INVENTION

The object of the present invention is to provide a filter device which effectively removes air and impurities such as solid particles contained in a liquid such as a medicine, prevents the air in the medicine from flowing into an extension tube connected to the filter device, and ensures a maximum surface area of a hydrophilic filter for filtering off solid particles such as glass fragments so that a flow rate of a medicine passing through the filter device does not decrease; and a liquid injection apparatus including such a filter device.

In addition, another object of the present invention is to provide a filter device which may prevent impurities of adhesive components from flowing into the filter device and/or a capillary tube when the capillary tube in the extension tube is sealably connected to the filter device by an adhesive using a conventional method; and a liquid injection apparatus including such a filter device.

DETAILED DESCRIPTION OF INVENTION

According to the present invention, a filter device connected to a liquid supply line to filter and discharge an introduced liquid comprises:

an inflow tube having an inflow hole communicating with the liquid supply line and allowing a liquid introduced through the inflow hole to flow into an internal space of the filter device;

a filter housing communicating with the inflow tube and communicating with the outside;

an outlet tube having an outlet hole communicating with the filter housing, the outlet tube being disposed at a location opposite to the inflow tube, the outlet tube being spaced apart from the inflow tube substantially in parallel therewith to define a vertical space in the filter housing, the outlet tube allowing the liquid discharged from the filter housing to be transported to the outside;

a hydrophilic filter located between the inflow tube and the vertical space in the filter housing, the hydrophilic filter filtering off solid impurities in the liquid introduced through the inflow hole;

at least one hydrophobic filter located corresponding to at least one gas discharge hole provided in the filter housing, the hydrophobic filter allowing gas in the introduced liquid to be discharged to the outside before and/or after the liquid passes through the hydrophilic filter; and a blocking member for preventing gas in the liquid passing through the hydrophilic filter from flowing into the outlet tube, the blocking member being installed in the filter housing to block the outlet tube, the blocking member having a longitudinal passage formed in a center portion thereof so that the liquid is introduced into the outlet tube through the passage and discharged therefrom.

In one embodiment of the filter device according to the present invention, the filter housing may include an upper filter housing and a lower filter housing, which are detachably coupled. For example, the upper filter housing may be connected to the outlet tube, and the lower filter housing may be connected to the inflow tube.

In one embodiment of the filter device according to the present invention, a ring-shaped protrusion protruding upward or a ring-shaped concave portion may be formed in an upper surface of the lower filter housing, and a ring-shaped concave portion or a ring-shaped protrusion protruding downward may be correspondingly formed in a lower surface of the upper filter housing. The filter housing may be coupled by fitting the protrusion or concave portion of the lower filter housing to the corresponding concave portion or protrusion of the upper filter housing. At this time, the hydrophilic filter is located and fixed between an inner surface of the protrusion or concave portion of the lower filter housing and an inner surface of the concave portion or protrusion of the upper filter housing. Therefore, the hydrophilic filter divides the inside of the filter housing into an upper filter housing space and a lower filter housing space.

In one embodiment of the filter device according to the present invention, a transverse cross-sectional area of the vertical space in the filter housing is sized so that the hydrophilic filter is transversely located therein. Preferably, the larger the transverse cross-sectional area of the vertical space in the filter housing and the surface area of the hydrophilic filter are, the better they are. It allows the hydrophilic filter to filter off solid impurities P and prevents the flow rate of the liquid introduced through the inflow tube from being lowered.

In one embodiment of the filter device according to the present invention, at least one gas discharge hole may be formed in the upper filter housing and/or the lower filter housing.

Further, in one embodiment of the filter device according to the present invention, a gas discharge portion is provided in an inner or outer portion of the filter housing having the gas discharge hole formed therein, the gas discharge portion including the hydrophobic filter corresponding to the gas discharge hole and a fixing means for fixing the hydrophobic filter to the inner or outer portion of the filter housing and having a hole for discharging the gas to the outside.

Specifically, a filter seating portion protruding in a ring shape may be formed in the outer portion of the filter housing having the gas discharge hole formed therein, and the hydrophobic filter may be seated on the filter seating portion. In addition, a ring-shaped groove is formed around the filter seating portion, and a protrusion with a shape conforming to the ring-shaped groove is formed on the fixing means of the gas discharge portion so that the hydrophobic filter is fixed without escape. Therefore, if the protrusion of the fixing means of the gas discharge portion is inserted into the ring-shaped groove, the hydrophobic filter is fixed without escape. Thus, in one embodiment of the filter device according to the present invention, the gas in the liquid introduced into the filter housing is discharged to the outside through at least one gas discharge hole formed in the filter housing, the hydrophobic filter, and the hole formed in the fixing means of the gas discharge portion.

As an alternative, a depressed filter seating portion may be formed in the inner portion of the filter housing having the air discharge hole formed therein, and the hydrophobic filter may be seated on the filter seating portion. In addition, a stepped insert portion is formed around the filter seating portion, and the fixing means of the gas discharge portion is stepwise formed corresponding to the stepped insert portion so that the hydrophobic filter is fixed without escape. Therefore, if the fixing means of the stepped gas discharge portion is inserted into the stepped insert portion, the hydrophobic filter is fixed without escape. Thus, in another embodiment of the filter device according to the present invention, the gas in the liquid introduced into the filter housing is discharged to the outside through the hole formed in the fixing means of the gas discharge portion, the hydrophobic filter, and at least one gas discharge hole formed in the filter housing.

In one embodiment of the filter device according to the present invention, the blocking member may include a front end contacting with the liquid in the filter housing, an outlet tube coupling portion coupled to the outlet tube, and a distal end contacting with an extension tube connected to the outlet tube.

In the present invention, by means of the configuration of the blocking member, it is possible to effectively prevent the gas in the liquid from flowing into the outlet tube. That is, when the injectable liquid flowing in a wide space of the filter housing space is introduced into the passage of the blocking member which is abruptly narrowed, once the injectable liquid comes into contact with the front end of the blocking member, the liquid component L of the injectable liquid may be introduced into the outlet tube through the passage and be discharged therefrom. However, once the liquid component of the injectable liquid is in contact with the front end of the blocking member, the gas G in the injectable liquid is not introduced into the longitudinal passage of the blocking member since the longitudinal passage of the blocking member is narrow. Therefore, the filter device of the present invention may effectively remove the gas G and impurities such as solid particles P contained in the injectable liquid and prevent the gas G in the injectable liquid from flowing into the extension tube connected to the filter device.

Optionally, the front end may have a tapered shape the size of which gradually decreases toward the inside of the filter housing, and an inner diameter of the front end may be smaller than that of the distal end. In other words, the longitudinal passage of the blocking member may have a tapered shape in which the inner diameter gradually increases from the inside of the filter housing toward the outlet tube. For example, the longitudinal passage at the front end of the blocking member may have an inner diameter of about 0.4 mm, and the longitudinal passage at the distal end of the blocking member may have an inner diameter of about 0.8 mm. In the case where the longitudinal passage of the blocking member has a tapered shape in which the inner diameter gradually increases from the inside of the filter housing toward the outlet tube as described above, there are additional advantages in that it is possible to allow the liquid to be introduced into the outlet tube and easily discharged therefrom and to allow the air to be effectively blocked.

In addition, an anti-escaping projection may be formed on an inner wall of the outlet tube, a ring-shaped groove is optionally formed in the outlet tube coupling portion of the blocking member, and the distal end of the blocking member is formed to have an outer diameter conforming to an inner diameter of the outlet tube. Therefore, the groove of the outlet tube coupling portion of the blocking member may be coupled to the anti-escaping projection of the outlet tube in a catching manner, and the distal end of the blocking member may be formed to conform to an inner diameter of the outlet tube so as to prevent the blocking member from escaping from the outlet tube.

However, the present invention is not limited thereto, but the blocking member may have various shapes. For example, the front end may have a long cylindrical shape, or the front end may have the inner diameter substantially identical to the inner diameter of the distal end. Meanwhile, in this case, the outlet tube coupling portion of the blocking member is formed to have an outer diameter conforming to the inner diameter of the anti-escaping projection, and the distal end of the blocking member is formed to have an outer diameter conforming to the inner diameter of the outlet tube.

In one embodiment of the filter device according to the present invention, the distal end of the blocking member may be in direct contact with the extension tube connected to the outlet tube or in close surface contact with a capillary tube installed in the extension tube.

For example, the capillary tube may be fixedly supported in the extension tube, a projection through which the liquid introduced from the capillary tube can pass may be installed in the extension tube, and the capillary tube may be inserted into an O-shaped ring and be in close contact with and fixed to a coupling portion between the outlet tube and the extension tube. Since the capillary tube is sealably coupled to the filter device by the close contact between the distal end of the blocking member and the capillary tube, it is not needed to couple the capillary tube to the tube of the filter device using a separate adhesive. However, the present invention is not limited thereto, but various coupling types may be used for coupling the extension tube to the distal end of the outlet tube, as is apparent to those having ordinary skill in the art.

In one embodiment of the filter device according to the present invention, the blocking member may be located in the upper filter housing. Therefore, the front end of the blocking member may be located to protrude into the upper filter housing.

In one embodiment of the filter device according to the present invention, the blocking member is preferably made of silicone or plastic material. More preferably, the silicone material is used.

In addition, a liquid injection apparatus according to the present invention includes the filter device as described above.

Advantageous Effects

According to the present invention, there are advantages in that the filter device can effectively remove air and impurities such as solid particles contained in a liquid such as a medicine, prevent the air in the medicine from flowing into an extension tube connected to the filter device, and ensure a maximum surface area of a hydrophilic filter for filtering off solid particles such as glass fragments so that a flow rate of a medicine passing through the filter device does not decrease.

In addition, it is possible to prevent impurities of adhesive components from flowing into the filter device and/or the capillary tube when the capillary in the extension tube is sealably connected to the filter device by an adhesive using a conventional method.

BRIEF DESCRIPTION OF DRAWINGS

The above and other technical subjects and features of the present invention will be more apparent to those having ordinary skill in the art by the following description on the embodiments of the present invention with reference to the accompanying drawings, in which:

FIGS. 5 (a) and (b) are respectively a perspective view and a longitudinal sectional view showing a blocking member 30 housed in the filter device 100 according to the first embodiment of the present invention;

FIGS. 6 (a) and (b) are respectively a perspective view and a longitudinal sectional view showing an O-shaped ring 50 inserted into a capillary tube 40 housed in an extension tube 60 connected to an outlet tube 22 of the filter device 100 according to the first embodiment of the present invention;

EXAMPLES

Hereinafter, preferred embodiments according to the present invention will be described in detail with reference to the accompanying drawings. The following embodiments of the present invention are just to implement the present invention and are not intended to limit or restrict the scope of the present invention. All techniques easily conceivable by those skilled in the art from the detailed descriptions and embodiments of the present invention are interpreted as belonging to the scope of the present invention. The references cited herein are incorporated herein by reference.

Figure 1:
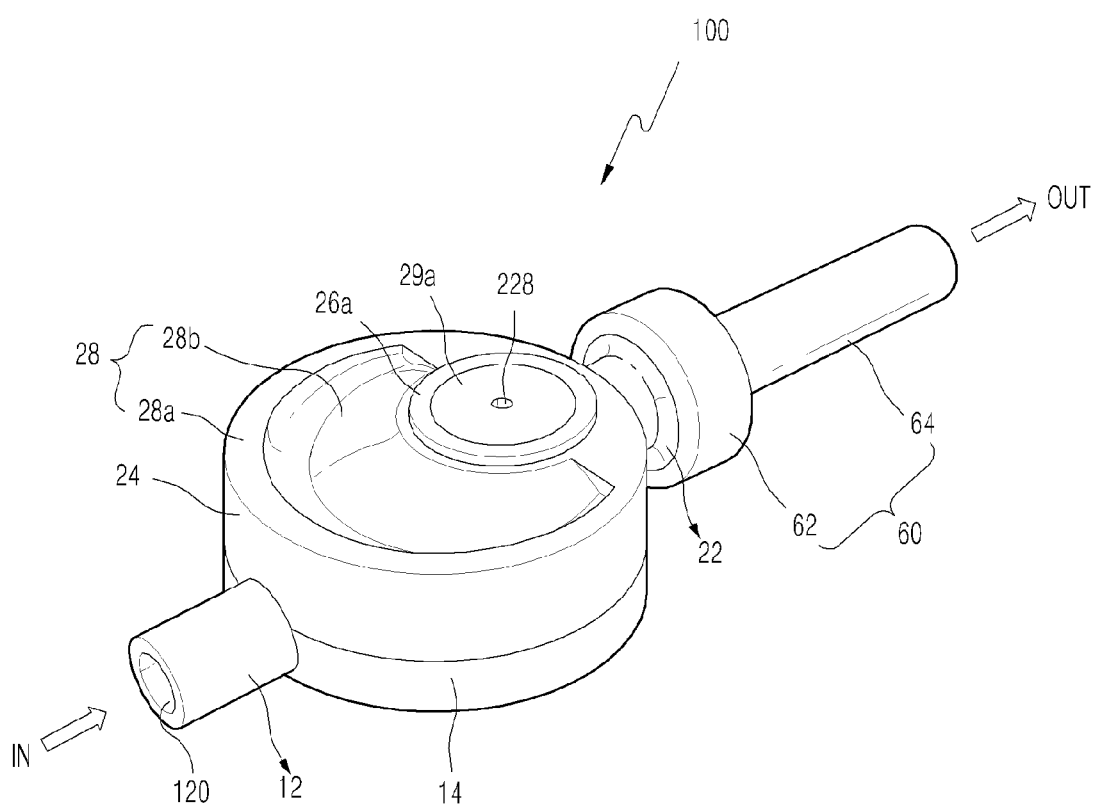
FIG. 1 is a perspective view showing a filter device 100 in an assembled state according to a first embodiment of the present invention.
Figure 2:
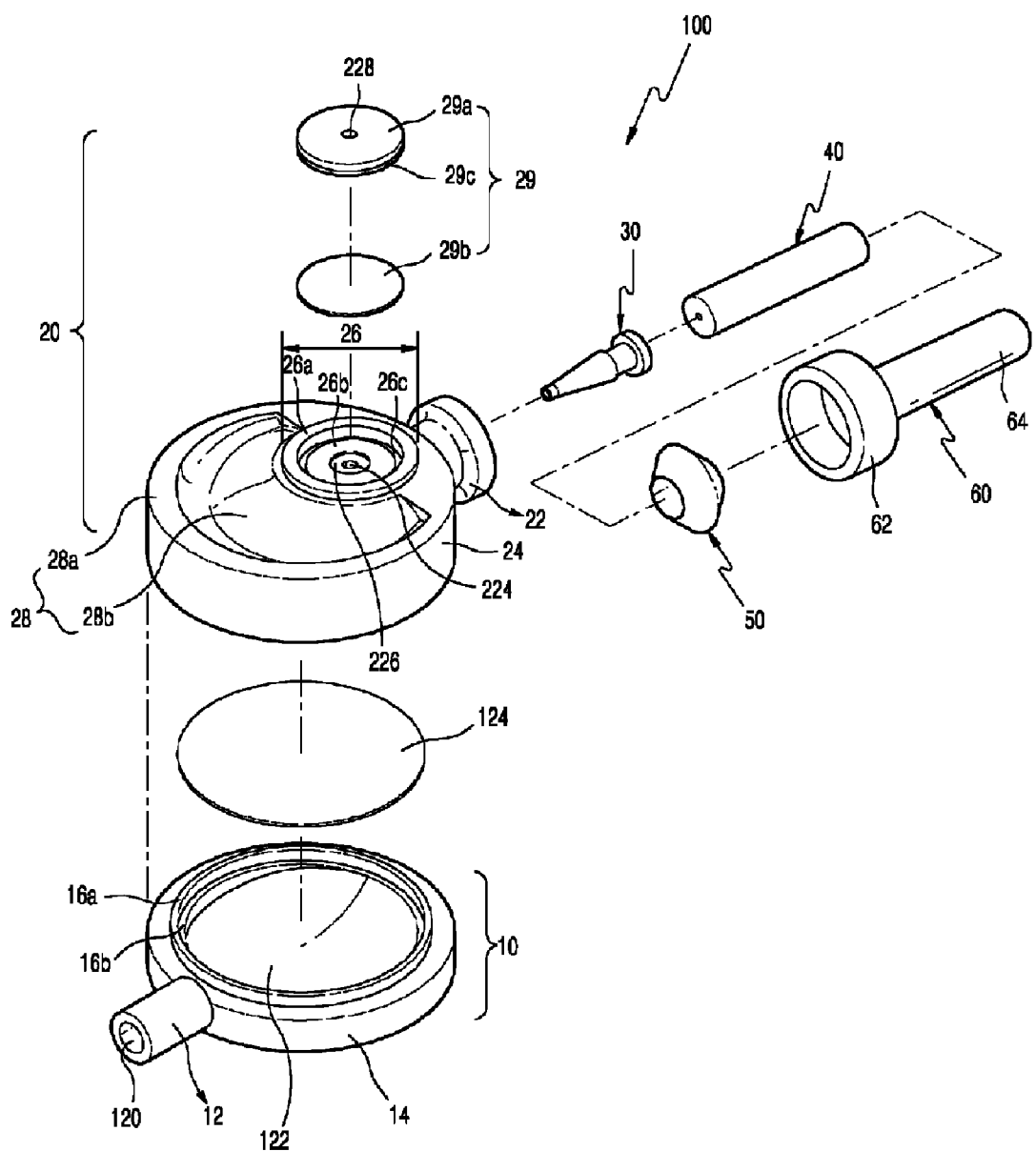
FIG. 2 is an exploded perspective view showing the filter device 100 in a dissembled state according to the first embodiment of the present invention.

A filter device 100 according to a first embodiment of the present invention as shown in FIGS. 1 to 6 is installed between a tube connected to and extending from an IV (intravenous) bottle and an extension tube or a distal end connector to which an injection needle or catheter inserted into a patient is detachably coupled. As shown in FIG. 2, the filter device 100 of the first embodiment of the present invention generally includes an inflow tube 12, a lower filter housing 10, a hydrophilic filter 124, an upper filter housing 20 having a gas discharge hole 224, an outlet tube 22, and a blocking member 30. In addition, the upper filter housing 20 of the filter device 100 according to the first embodiment of the present invention includes a gas discharge portion 29 corresponding to the gas discharge hole 224, wherein gas discharge portion 29 includes a hydrophobic filter 29b and a fixing means 29a for fixing the hydrophobic filter 29b to the outside of the upper filter housing 20 and having a hole 228 for exhausting gas to the outside.

Figure 3:
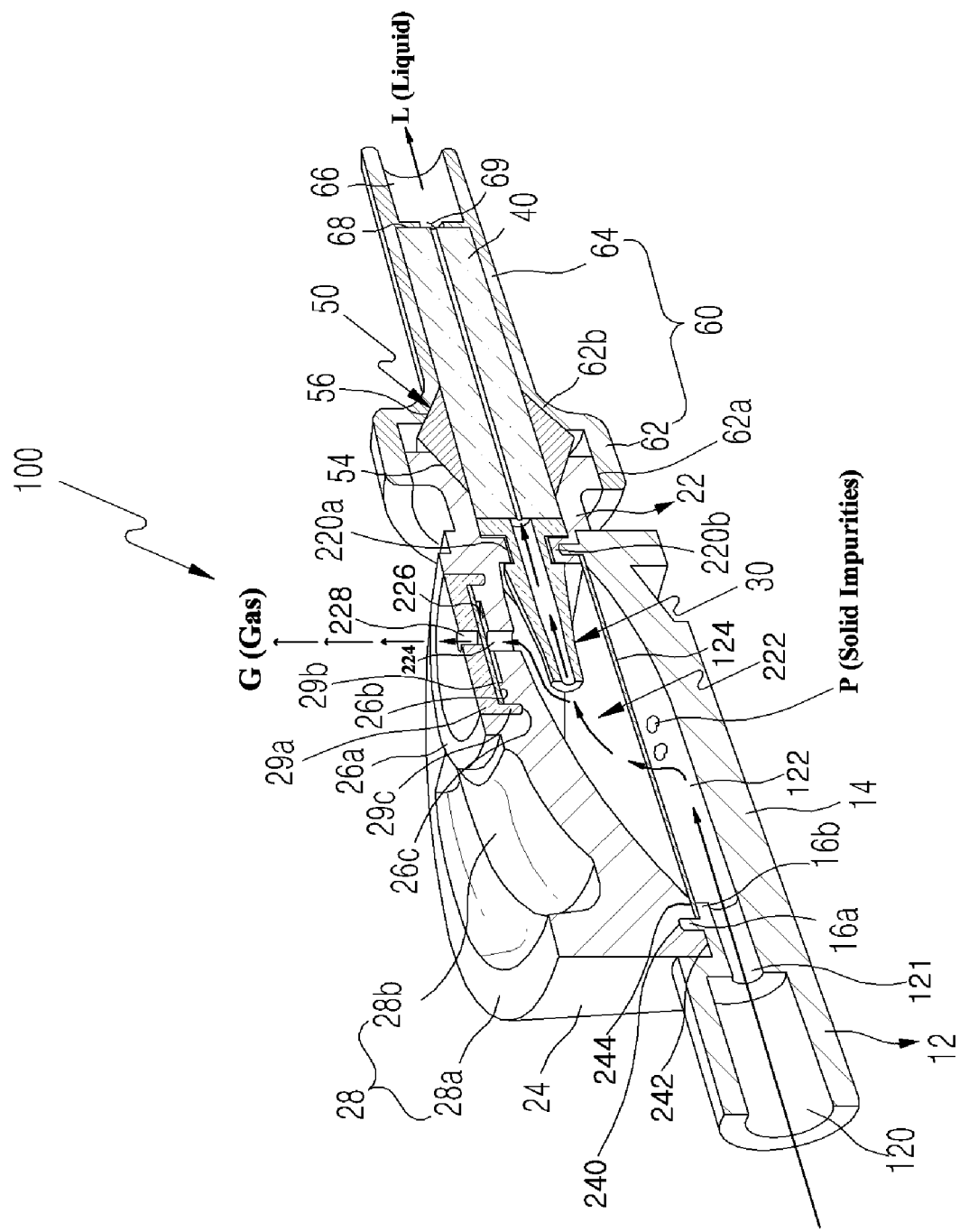
FIG. 3 is a longitudinal sectional view showing the filter device 100 in an assembled state according to the first embodiment of the present invention.

As shown in FIGS. 1 to 4, the inflow tube 12 has an inflow hole 120 at one end thereof to communicate with an inflow-side liquid supply line, and a passage 121 at the other end thereof to introduce an injectable liquid introduced through the inflow hole 120 into the lower filter housing 10. As shown in FIG. 3, the passage 121 is formed to be narrower than the inflow hole 120, but it will be understood by those having ordinary skill in the art that the present invention is not limited thereto.

As shown in FIG. 2, in the filter device 100 according to the first embodiment of the present invention, the filter housing is composed of the lower filter housing 10 and the upper filter housing 20 which can be coupled to or detached from each other. The lower filter housing 10 and the upper filter housing 20 communicate with the inflow tube 12 and the outlet tube 22, respectively. In other words, as shown in FIG. 4, it could be found that the lower filter housing 10 is connected to the inflow tube 12, and the upper filter housing 20 is connected to the outlet tube 22 to communicate therewith.

Figure 4:
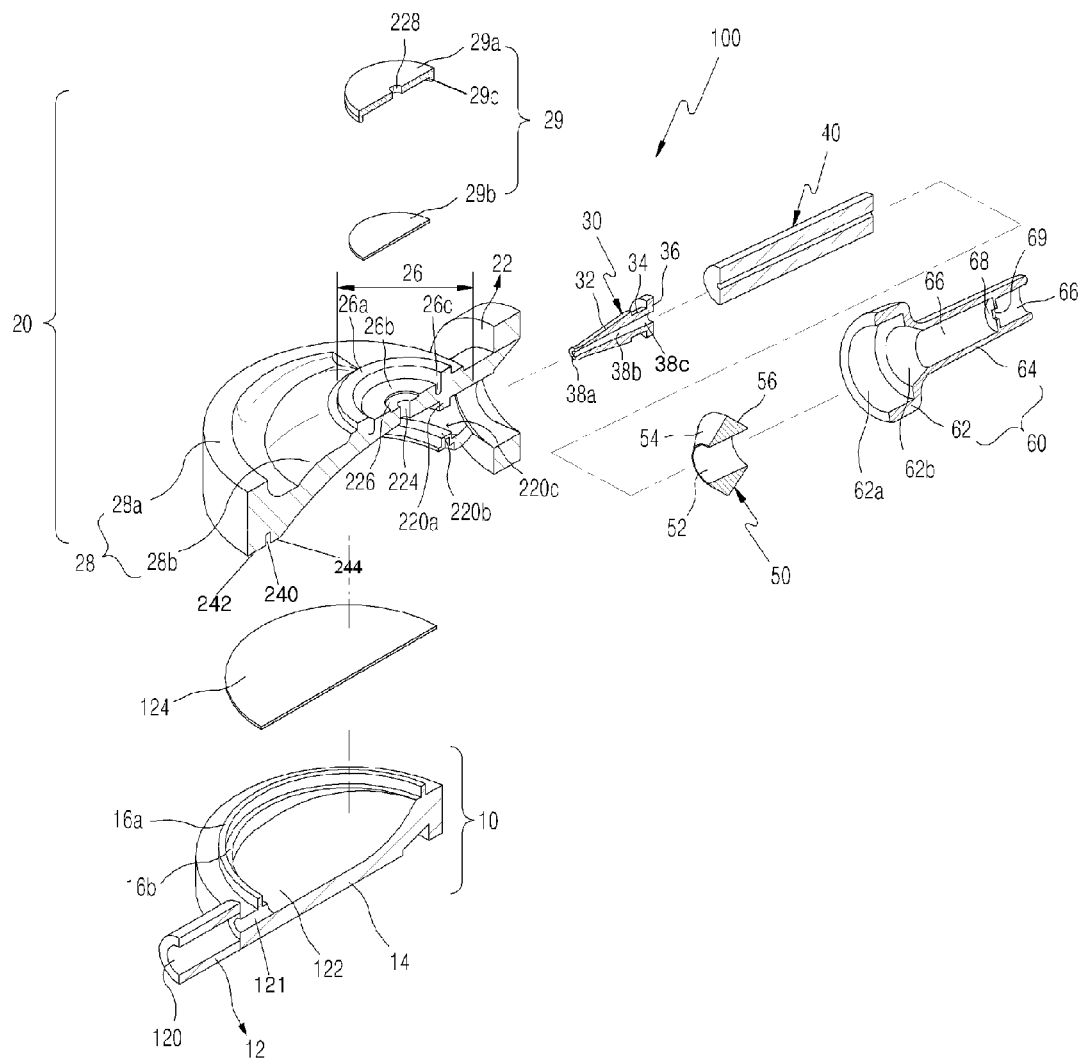
FIG. 4 is a longitudinal sectional view showing the filter device 100 in a dissembled state according to the first embodiment of the present invention.

As shown in FIGS. 2 to 4, the lower filter housing 10 has a disk-shaped body 14. The inflow tube 12 is connected to one side of the body 14, and a ring-shaped protrusion 16a protruding upward is formed on the upper surface of the body 14.

The upper filter housing 20 also has a disk-shaped body 24, and the outlet tube 22 is connected to one side of the body 24 (see FIGS. 2 and 3). The outlet tube 22 has an outlet hole 220c communicating with the upper filter housing 20 (see FIG. 4). The outlet tube 22 is disposed at a location opposite to the inflow tube 12 and vertically spaced apart from the inflow tube 12 in parallel thereto so that a space (i.e., a lower filter housing space 122 and an upper filter housing space 222) is vertically formed in the filter housing. The outlet tube 22 transports to the outside the injectable liquid flowing through the inflow hole 120, the lower filter housing space 122, the hydrophilic filter 124, the upper filter housing space 222 and the blocking member 30.

In addition, as shown in FIGS. 3 and 4, a ring-shaped concave portion 240 is formed in the lower surface of the upper filter housing 20. The protrusion 16a of the lower filter housing 10 is fitted into the concave portion 240 of the upper filter housing 20, thereby the filter housing detachably coupled to each other. At this time, the hydrophilic filter 124 is fixedly located between an inner side 16b of the protrusion 16a of the lower filter housing 10 and an inner side 244 of the concave portion 240 of the upper filter housing 20. However, the filter hosing of the present invention is not limited to the detachably coupled upper and lower filter housings, but various modifications where the filter housing is integrally formed are also included in the scope of the present invention, as apparent to those skilled in the art.

Therefore, as shown in FIG. 3, the hydrophilic filter 124 divides the inside of the filter housing into the upper filter housing space 222 and the lower filter housing space 122. In addition, the hydrophilic filter 124 filters off solid impurities P such as glass fragments in the injectable liquid introduced through the inflow hole 120 at the lower filter housing space 122, and then the injectable liquid is delivered to the upper filter housing space 222 (see FIG. 3). Meanwhile, any one well known in the art and commercially available if it filters off solid impurities P and allows liquid to pass may be used as the hydrophilic filter 124.

Meanwhile, in the filter device 100 according to the first embodiment of the present invention, a transverse cross-sectional area of the vertical space 122 in the lower filter housing 10 should be sized so that the hydrophilic filter 124 is transversely located therein. Preferably, the larger the transverse cross-sectional area of the vertical space 122 in the lower filter housing 10 and the surface area of the hydrophilic filter 124 are, the better they are. By doing so, while the hydrophilic filter 124 filters off solid impurities P, the flow rate of the injectable liquid introduced through the inflow tube 12 is not lowered.

In addition, in the filter device 100 according to the first embodiment of the present invention, the upper surface 28 of the upper filter housing 20 is composed of a protruding rim portion 28a and a depressed portion 28b, and the upper surface 28 is formed with at least one gas discharge hole 224 (see FIGS. 2 and 3).

The upper filter housing 20 has a gas discharge portion receiving portion 26, which is coupled to the gas discharge portion 29, provided around a location where the gas discharge hole 224 is formed. The gas discharge portion receiving portion 26 has a filter seating portion 26b having a ring shape and protruding upwards formed around the gas discharge hole 224, and the hydrophobic filter 29b of the gas discharge portion 29 is seated on the filter seating portion 26b.

In addition, in the gas discharge portion receiving portion 26, a ring-shaped additional protrusion 26a is formed around the filter seating portion 26b to protrude in a spaced relation therewith by a certain interval. By doing so, a ring-shaped groove 26c is formed between the filter seating portion 26b and the ring-shaped additional protrusion 26a in the gas discharge portion receiving portion 26 so that the hydrophobic filter 29b is not detached from but fixed to the gas discharge portion receiving portion 26, and a protrusion 29c with a shape conforming to the ring-shaped groove 26c is formed on the fixing means 29a having the hole 228 as described above to extend downwards in a ring shape. Therefore, if the protrusion 29c of the fixing means 29a of the gas discharge portion 29 is inserted into the ring-shaped groove 26c formed in the gas discharge portion receiving portion 26, the hydrophobic filter 29b of the gas discharge portion 29 may be fixed without escape.

As shown in FIG. 3, gas G in the injectable liquid, which passes through the hydrophilic filter 124 so that solid impurities P are filtered off, is discharged to the outside from the upper filter housing space 222 through at least one gas discharge hole 224 formed in the upper surface of the upper filter housing 20, the space 226 between the gas discharge hole 224 and the hydrophobic filter 29b, the hydrophobic filter 29b, and the hole 228 formed in the fixing means 29a. Meanwhile, any one well known in the art and commercially available if it does not allow liquid L to pass but allows the gas G to pass may be used as the hydrophobic filter 29b.

Next, the filter device 100 according to the first embodiment of the present invention includes the blocking member 30 for preventing the gas G in the injectable liquid from flowing into the outlet tube 22. As described above, there is a problem in that in a conventional filter device, the gas in the injectable liquid is not entirely discharged through the air discharge hole after passing through the gas permeable filter, i.e., the hydrophobic filter but partially introduced into the extension tube connected to a patient.

In the filter device 100 according to the first embodiment of the present invention, the blocking member 30 is installed in the upper filter housing 20 to block the outlet tube 22. Passages 38a, 38b and 38c are formed at the center portion of the blocking member 30 in its longitudinal direction so that the injectable liquid L flows through the passages into the outlet tube 22 and then is discharged therefrom (see FIGS. 3 to 5).

As shown in FIGS. 3 to 5, the blocking member 30 is located in the upper filter housing 20. The blocking member 30 includes a front end 32 contacting with the injectable liquid in the upper filter housing 20, an outlet tube coupling portion 34 coupled to the outlet tube 22, and a distal end 36 contacting with the extension tube connected to the outlet tube 22. Optionally, in the filter device 100 according to the first embodiment of the present invention, a capillary tube 40 may be installed in the extension tube 60, and at this time, the distal end 36 of the blocking member 30 comes into contact with the capillary tube 40.

In the filter device 100 according to the first embodiment of the present invention, the front end 32 of the blocking member 30 may have a tapered shape the size of which gradually decreases toward the inside of the upper filter housing 20, and the inner diameter of the front end 32 may be smaller than the inner diameter of the distal end 36 (see FIG. 5). However, the present invention is not limited thereto, but the blocking member may have various shapes. For example, the front end 32 may have a long cylindrical shape, the inner diameter of the front end 32 may be substantially identical to that of the distal end 36, and the like.

In the filter device 100 according to the first embodiment of the present invention, such a blocking member 30 may effectively prevent the gas in the injectable liquid from flowing into the outlet tube 22. In other words, when the injectable liquid flowing in a wide space of the upper filter housing space 222 is introduced into the passage of the blocking member 32 which is abruptly narrowed, once the injectable liquid comes into contact with the front end 32 of the blocking member 30, the liquid component L of the injectable liquid may be introduced into the outlet tube 22 through the passages 38a, 38b and 38c and be discharged therefrom. However, once the liquid component of the injectable liquid is in contact with the front end 32 of the blocking member 30, the gas G in the injectable liquid is not introduced into the longitudinal passages since the longitudinal passages 38a, 38b and 38c of the blocking member 30 are narrow. Therefore, the filter device 100 of the present invention may effectively remove the gas G and impurities such as solid particles P contained in the injectable liquid and prevent the gas G in the injectable liquid from flowing into the extension tube 60 connected to the filter device.

In addition, as shown in FIGS. 4 and 5, the longitudinal passages 38a, 38b and 38c of the blocking member 30 may have a tapered shape in which the inner diameter gradually increases from the inside of the upper filter housing 20 toward the outlet tube 22. For example, the longitudinal passage at the front end 32 of the blocking member 30 may have an inner diameter d1 of about 0.4 mm, and the longitudinal passage at the distal end 36 of the blocking member 30 may have an inner diameter d2 of about 0.8 mm (see FIG. 5). In the case where the longitudinal passages 38a, 38b and 38c of the blocking member 30 have a tapered shape in which the inner diameter gradually increases from the inside of the upper filter housing 20 toward the outlet tube 22, the liquid L may be introduced into the outlet tube 22 and easily discharged therefrom, but the gas G is effectively blocked, which is an additional advantage.

However, the present invention is not limited to the dimension and shape of the blocking member 30 as described above, and modifications having various dimensions and shapes for identical or similar functions are also included in the scope of the present invention, as is apparent to those having ordinary skill in the art.

In addition, as shown in FIGS. 3 and 4, anti-escaping projections 220a and 220b are formed on the inner wall of the outlet tube 22, and a ring-shaped groove is formed in the outlet tube coupling portion 34 of the blocking member 30. Specifically, the groove of the outlet tube coupling portion 34 of the blocking member 30 can be coupled to the anti-escaping projections 220a and 220b of the outlet tube 22 connected to the upper filter housing 20 in a catching manner and prevent the blocking member 30 from escaping from the outlet tube 22. In addition, with this configuration, it is possible to prevent the gas G in the injectable liquid from flowing into the outlet tube 22 through the outlet hole 220c and ultimately to effectively prevent the gas G from flowing into the extension tube 60.

However, the present invention is not limited thereto, and the front end 32 and the outlet tube coupling portion 34 of the blocking member 30 may have a long cylindrical shape.

In this case, the outlet tube coupling portion 32 of the blocking member 30 is formed to have an outer diameter conforming to the inner diameter of the anti-escaping projections 220a and 220b, and the distal end 36 of the blocking member 30 is formed to have an outer diameter conforming to the inner diameter of the outlet tube 22.

In addition, in the filter device 100 according to the first embodiment of the present invention as shown in FIG. 3, the distal end 36 of the blocking member 30 is in close surface contact with the capillary 40 installed in the extension tube 60.

As shown in FIG. 4, the extension tube 60 includes an enlarged portion 62 and an extension portion 64. The enlarged portion 62 of the extension tube 60 has a two-stepped shape, wherein the outermost stepped portion 62a is fitted around and closely coupled to the outer circumference of the outlet tube 22, and the inner stepped portion 62b is closely coupled to a rear surface 56 of an O-shaped ring 50, which will be described later (see FIG. 3). A passage 66 is formed in the extension portion 64 of the extension tube 60. In addition, the capillary tube 40 is fixedly supported in the extension tube 60, and a projection 68 through which the injectable liquid L from the capillary 40 can pass is installed in the extension tube 60. A small hole 69 is formed in the projection 68, so that the injectable liquid L passing through the capillary tube 40 is discharged through the small hole 69.

As shown in FIGS. 3 and 6, the capillary tube 40 is inserted into the hole 52 of the O-shaped ring 50. A front surface 54 of the O-shaped ring 50 comes into close contact with the rear inclined surface of the outlet tube 22, and the rear surface 56 of the O-shaped ring 50 is closely coupled to the stepped portion 62b in the enlarged portion 62 of the extension tube 60. In addition, one end of the capillary tube 40 inserted into the hole 52 of the O-shaped ring 50 is received in the outlet tube 22, and the other end thereof is inserted into the passage 66 of the extension portion 64 of the extension tube 60 and also supported and fixed by the projection 68. At this time, the one end of the capillary tube 40 inserted into the hole 52 of the O-shaped ring 50 is securely fixed due to the fixation of the O-shaped ring 50 and therefore comes into close contact with the distal end 36 of the blocking member 30 through the outlet tube 22. Since the capillary tube 40 is sealably coupled to the filter device 100 by the close contact between the one end of the capillary tube 40 inserted into the hole 52 of the O-shaped ring 50 and the distal end 36 of the blocking member 30, it is not needed to couple the capillary tube 40 to the tube of the filter device 100 using a separate adhesive.

Meanwhile, in the filter device 100 according to the first embodiment of the present invention, the blocking member 30 is preferably made of silicone or plastic material, more preferably silicone material.

Hereinafter, a filter device 100' according to a second embodiment, which is a modification of the filter device 100 according to the first embodiment of the present invention, will be described. Meanwhile, prior to the description of the second embodiment of the present invention, it should be noted that the same component as in the first embodiment is designated by the same reference symbol, and the details thereof will be partially omitted.

Figure 9:
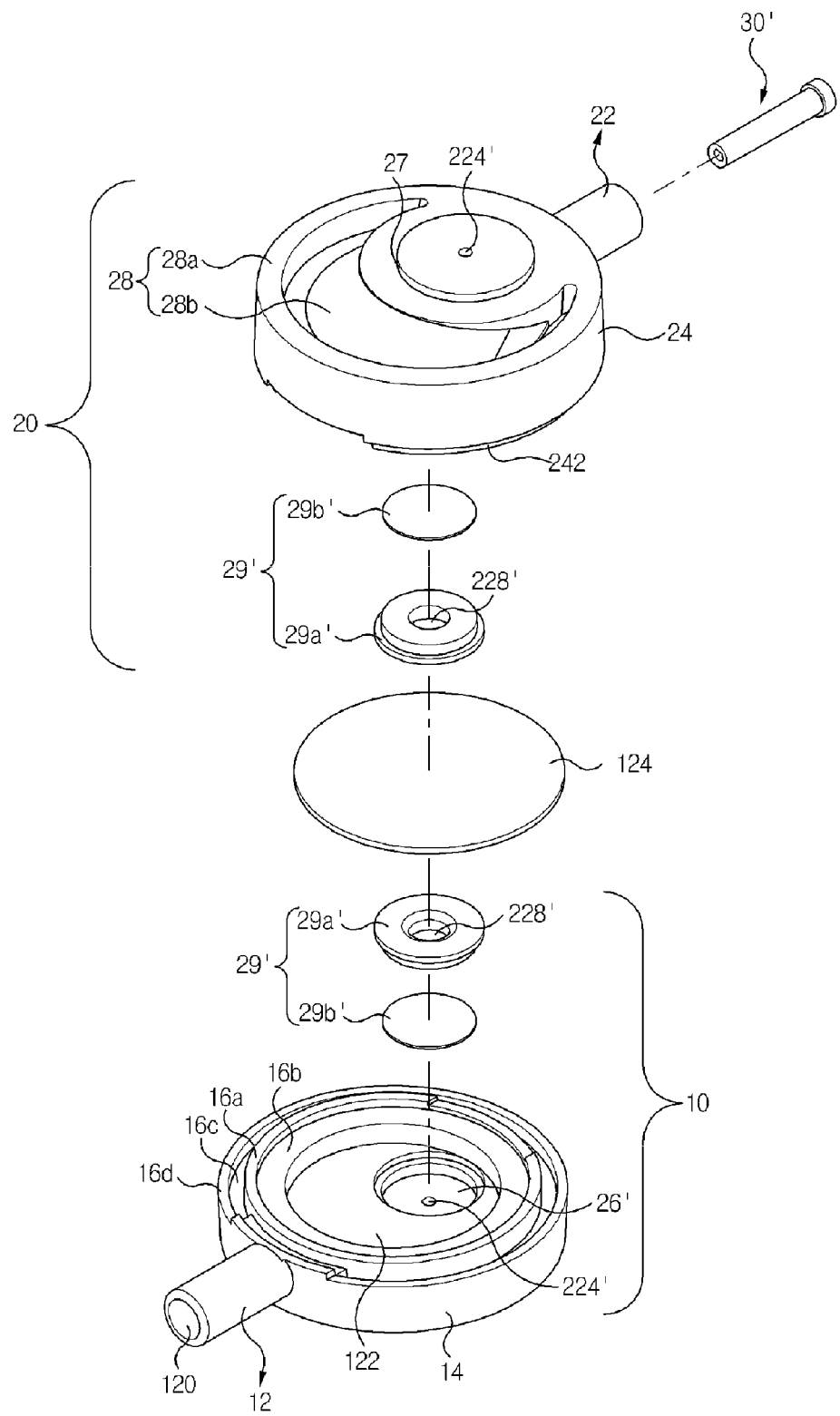
FIG. 9 is an exploded perspective view showing the filter device 100' in a dissembled state according to the second embodiment of the present invention.

The filter device 100' according to the second embodiment of the present invention as shown in FIGS. 7 to 11 is also installed between a tube connected to and extending from an IV bottle and an extension tube or a distal end connector to which an injection needle or catheter inserted into a patient is coupled. As shown in FIG. 9, the filter device 100' according to the second embodiment of the present invention generally includes an inflow tube 12, a lower filter housing 10 having a gas discharge hole 224' formed therein, a hydrophilic filter 124, an upper filter housing 20 having a gas discharge hole 224' formed therein, an outlet tube 22, and a blocking member 30'. In addition, each of the lower filter housing 10 and the upper filter housing 20 of the filter device 100' according to the second embodiment of the present invention is provided with a gas discharge portion 29' corresponding to the gas discharge hole 224', wherein the gas discharge portion 29' includes a hydrophobic filter 29b' and a fixing means 29a' having a hole 228' for exhausting gas to the outside and fixing the hydrophobic filter 29b' in each of the lower filter housing 10 and the upper filter housing 20.

The configuration of the inflow tube 12 and the inflow hole 120 and the configuration of the lower filter housing 10 and the upper filter housing 20 respectively connected to the inflow tube 12 and the outlet tube 22, which are shown in FIGS. 7 to 11, are substantially identical to those of the filter device 100 according to the first embodiment of the present invention, so that the details thereof will be omitted.

Figure 10:
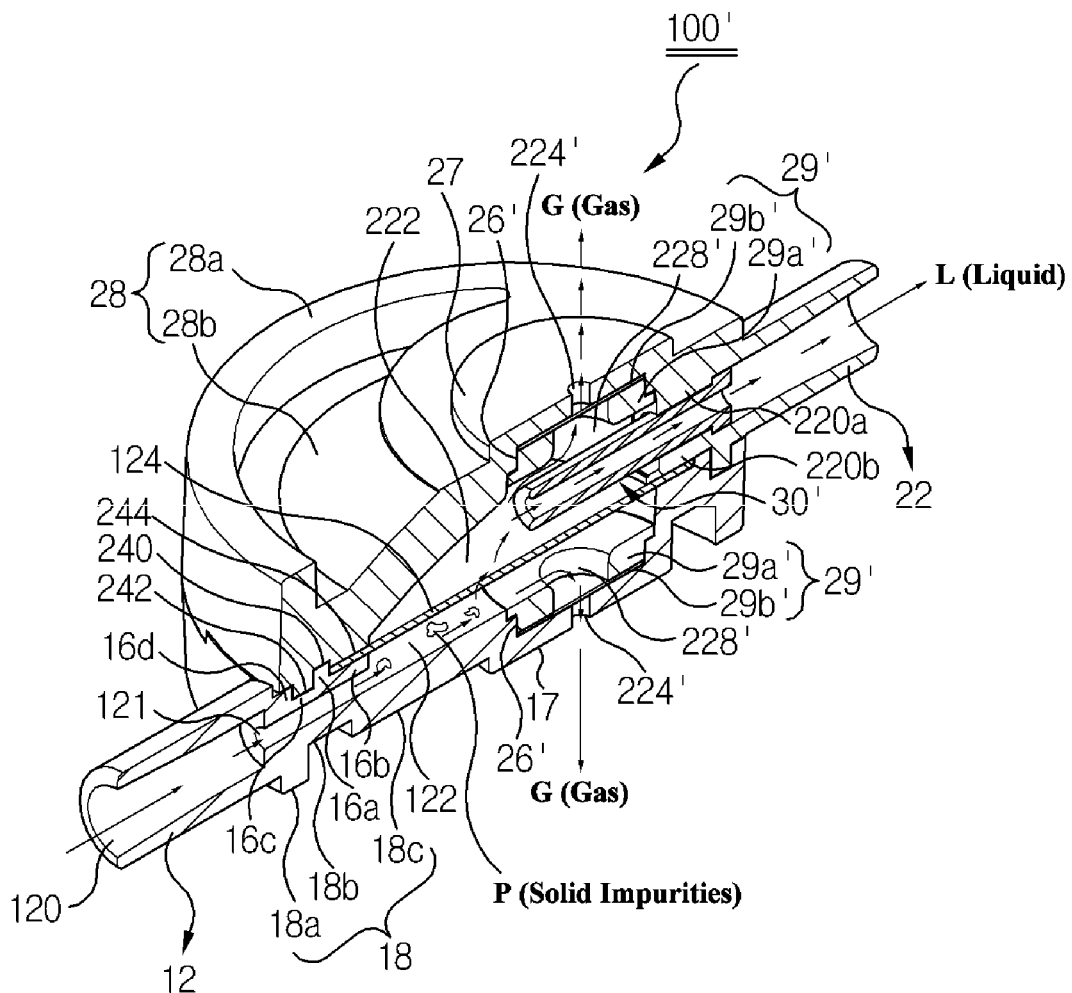
FIG. 10 is a longitudinal sectional view showing the filter device 100' in an assembled state according to the second embodiment of the present invention.
Figure 11:
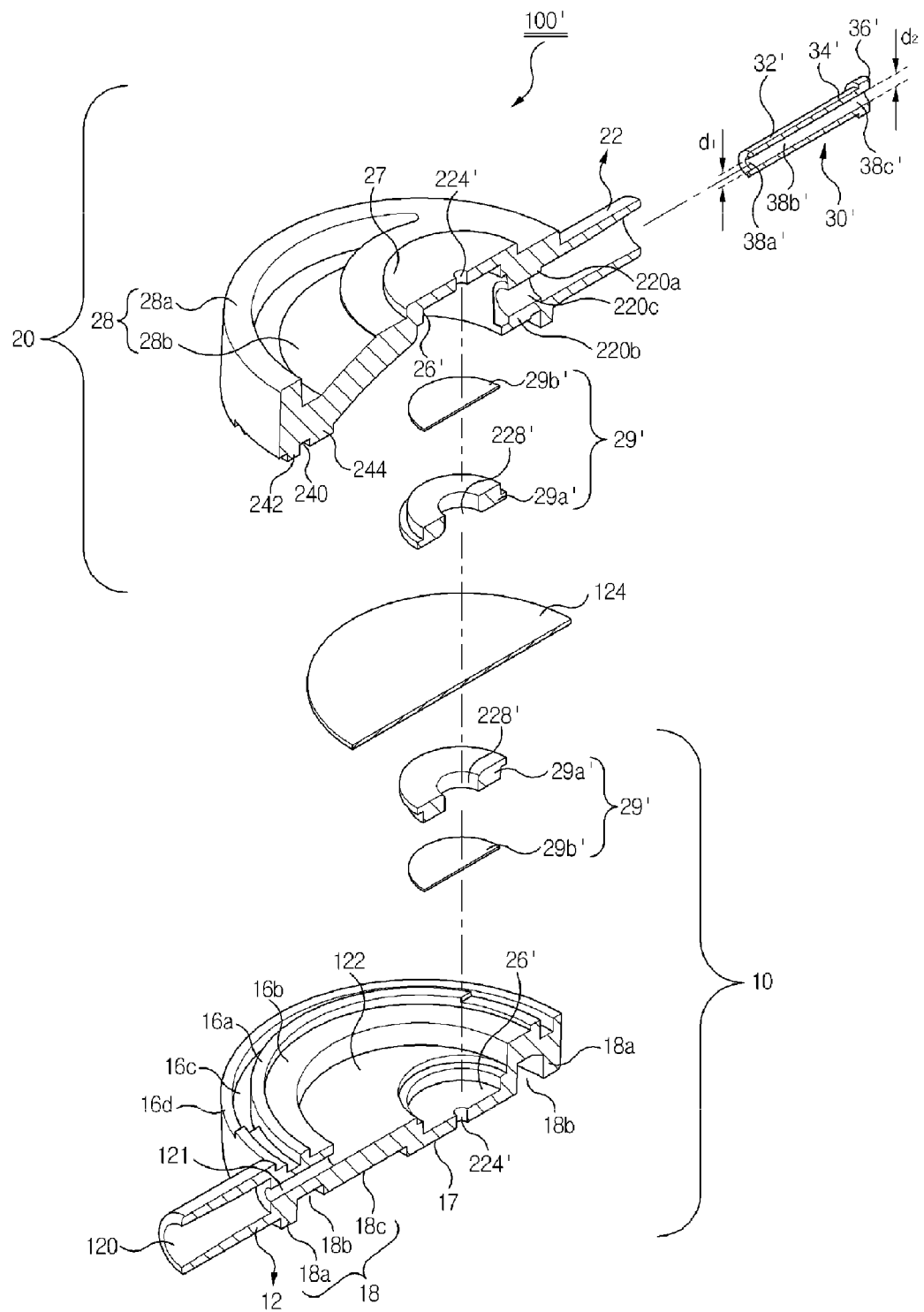
FIG. 11 is a longitudinal sectional view showing the filter device 100' in a dissembled state according to the second embodiment of the present invention.
Figure 12:
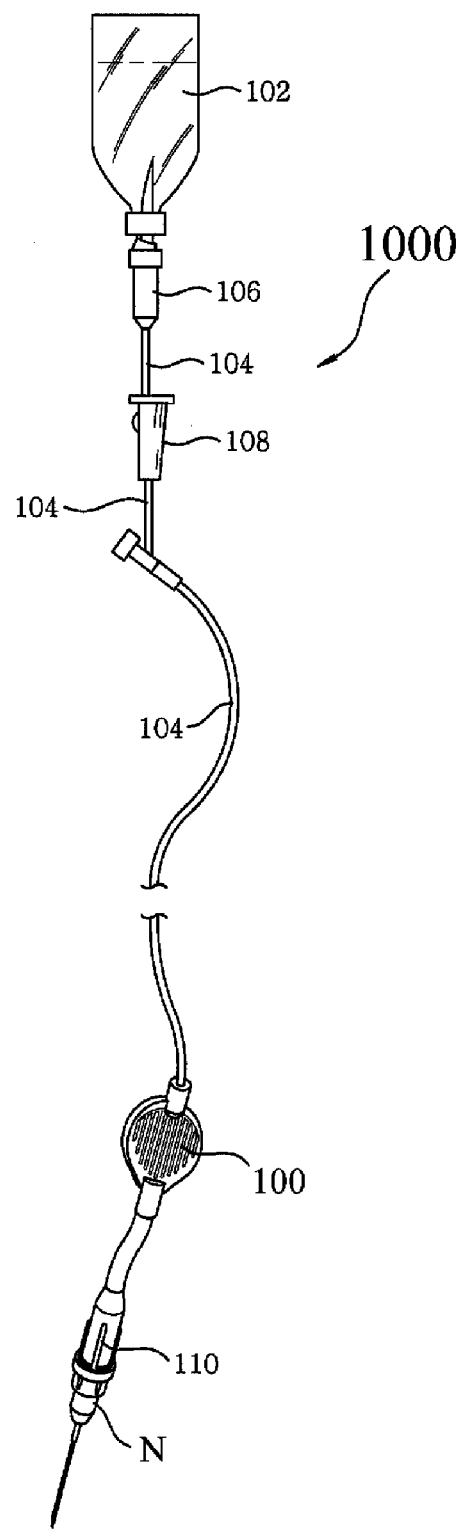
FIG. 12 is a perspective view showing a conventional liquid injection apparatus.
Figure 13:
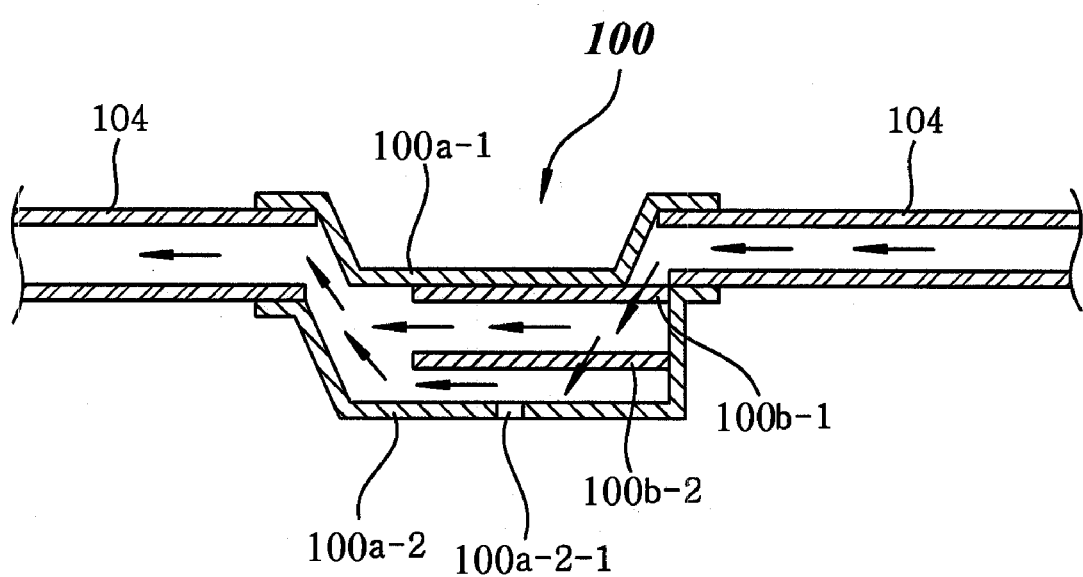
FIG. 13 is a sectional view showing a conventional filter device.

As shown in FIGS. 9 to 11, the lower filter housing 10 is provided with a disk-shaped body 14. The outermost portion of the body 14 is formed with a generally ring-shaped protrusion 16d, and a ring-shaped additional protrusion 16a protruding upwards is formed at a location spaced apart from the protrusion 16d of the outermost portion. Accordingly, a ring-shaped concave portion 16c is formed between the protrusions 16a and 16d.

As shown in FIGS. 9 to 11, the upper filter housing 20 is also provided with a disk-shaped body 24, and a generally ring-shaped concave portion 240 and a generally ring-shaped protrusion 242 are formed in the lower surface of the upper filter housing 20 from the inside thereof. The protrusion 16a and the concave portion 16c of the lower filter housing 10 described above are respectively fitted into the concave portion 240 and around the protrusion 242 of the upper filter housing 20 so that the filter housing may be detachably coupled to each other. At this time, a hydrophilic filter 124 is located and fixed between the inner surface 16b of the protrusion 16a of the lower filter housing 10 and the inner surface 244 of the concave portion 240 of the upper filter housing 20. However, the filter housing of the present invention is not limited to the detachably coupled upper and lower filter housings, but various modifications where the filter housing is integrally formed are also included in the scope of the present invention, as is apparent to those skilled in the art.

Therefore, as shown in FIG. 10, the hydrophilic filter 124 divides the inside of the filter housing into an upper filter housing space 222 and a lower filter housing space 122. In addition, the hydrophilic filter 124 filters off solid impurities P such as glass fragments in the injectable liquid introduced through the inflow hole 120 in the lower filter housing space 122 and then delivers the injectable liquid to the upper filter housing space 222. At this time, the gas G contained in the injectable liquid is removed in advance through the gas discharge hole 224' and the gas discharge portion 29' provided in the lower filter housing 10 (see FIG. 10). Meanwhile, any one well known in the art and commercially available if it filters off solid impurities P and allow liquid to pass may be used as the hydrophilic filter 124.

In addition, any one well known in the art and commercially available if it does not allow liquid L to pass but allows the gas G to pass may be used as the hydrophobic filter 29b' of the gas discharge portion 29'.

In addition, in the filter device 100' according to the second embodiment of the present invention, a lower surface 18 of the lower filter housing 10 is provided with a protruding rim portion 18a, a depressed portion 18b and a generally disk-shaped center portion 18c. Here, at least one gas discharge hole 224' is formed in the center portion 18c of the lower surface 18 (see FIGS. 8 to 11).

The lower filter housing 10 has a gas discharge portion receiving portion 26' formed around a location where the gas discharge hole 224' is formed. The gas discharge portion receiving portion 26' includes a filter seating portion which is depressed in a generally circular shape, and a stepped insert portion formed around the filter seating portion. In addition, the fixing means 29a' in which the hole 228' of the gas discharge portion 29' is formed is stepwise formed corresponding to the stepped insert portion of the gas discharge portion receiving portion 26'. Therefore, if the hydrophobic filter 29b' of the gas discharge portion 29' is seated on the filter seating portion of the gas discharge portion receiving portion 26' and the fixing means 29a' of the stepped gas discharge portion 29' is inserted into the stepped insert portion, the hydrophobic filter 26b' can be fixed without escape.

In addition, the gas G in the injectable liquid L primarily introduced into the lower filter housing 10 is discharged to the outside through the hole 228' formed in the gas discharge portion 29' installed in the lower filter housing 10, the hydrophobic filter 29b', and at least one gas discharge hole 224' formed in the lower filter housing 10. Thereafter, the hydrophilic filter 124 delivers the injectable liquid L to the space 222 of the upper filter housing 20, from which solid impurities P are filtered off and air is primarily removed.

Meanwhile, in the filter device 100' according to the second embodiment of the present invention, the transverse cross-sectional area of the vertical space 122 in the lower filter housing 10 should be sized so that the hydrophilic filter 124 is transversely located therein. Preferably, the larger the transverse cross-sectional area of the vertical space 122 in the lower filter housing 10 and the surface area of the hydrophilic filter 124 are, the better they are. By doing so, while the hydrophilic filter 124 filters off solid impurities P, the flow rate of the injectable liquid introduced through the inflow tube 12 is not lowered.

Figure 7:
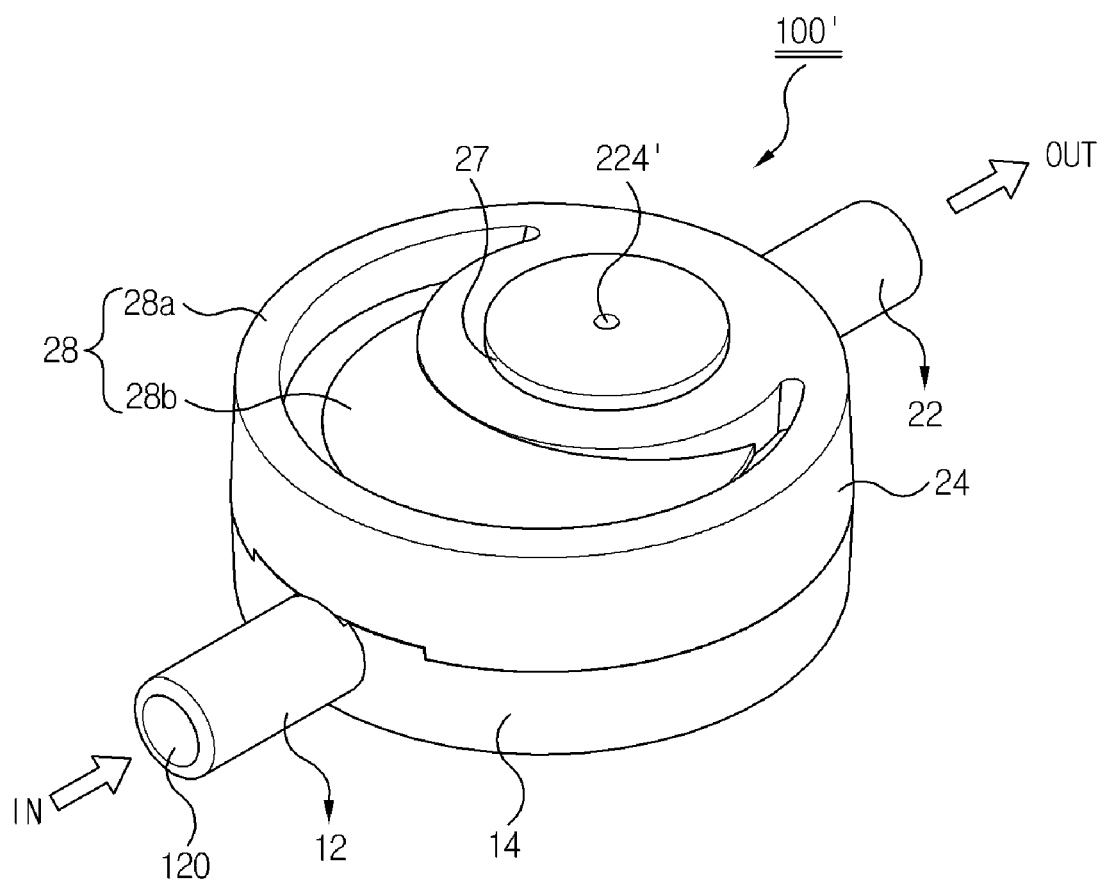
FIG. 7 is a top perspective view showing a filter device 100' in an assembled state according to a second embodiment of the present invention.
Figure 8:
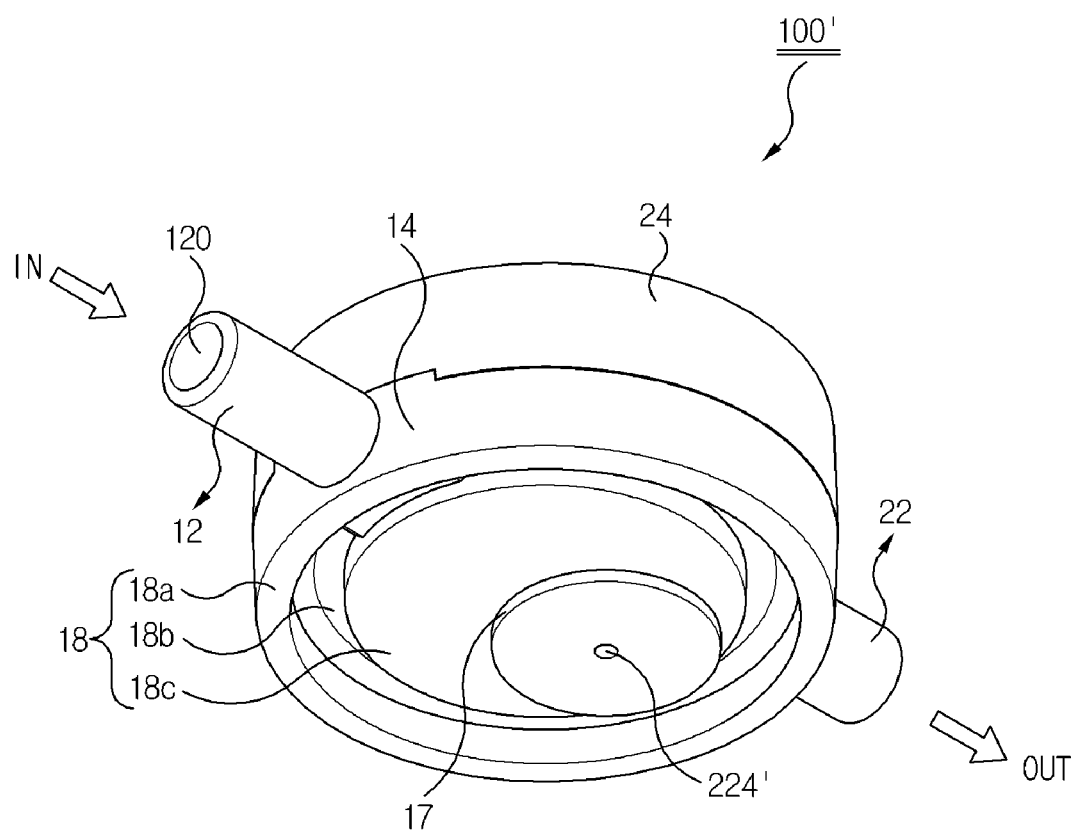
FIG. 8 is a bottom perspective view showing the filter device 100' in an assembled state according to the second embodiment of the present invention.

In addition, in the filter device 100' according to the first embodiment of the present invention, the upper surface 28 of the upper filter housing 20 is composed of a protruding rim portion 28a and a depressed portion 28b, and the upper surface 28 is formed with at least one gas discharge hole 224' (see FIGS. 7, 9 and 11).

The upper filter housing 20 also has a gas discharge portion receiving portion 26' formed around a location where the gas discharge hole 224' is formed. The gas discharge portion receiving portion 26' includes a filter seating portion depressed in a generally circular shape and a stepped insert portion formed around the filter seating portion. In addition, the fixing means 29a' in which the hole 228' of the gas discharge portion 29' is formed is stepwise formed corresponding to the stepped insert portion of the gas discharge portion receiving portion 26'. Therefore, if the hydrophobic filter 29b' of the gas discharge portion 29' is seated on the filter seating portion of the gas discharge portion receiving portion 26' and the fixing means 29a' of the stepped gas discharge portion 29' is inserted into the stepped insert portion, the hydrophobic filter 29b' can be fixed without escape.

Meanwhile, the injectable liquid introduced into the upper filter housing 20 through the hydrophilic filter 124 is in a state where solid impurities P are removed and gas G is primarily removed to some extent. However, residual air (gas) may remain therein. Therefore, as shown in FIG. 10, the residual gas G in the injectable liquid is discharged to the outside from the upper filter housing space 222 through the hole 228' formed in the fixing means 29a' of the gas discharge portion 20' installed in the upper filter housing 20, the hydrophobic filter 29b' and at least one gas discharge hole 224' formed in the upper filter housing 20.

Meanwhile, any one well known in the art and commercially available if it does not allow liquid L to pass but allows the gas G to pass may be used as the hydrophobic filter 29b' of the gas discharge portion 29'.

Next, the filter device 100' according to the second embodiment of the present invention includes a blocking member 30' for preventing gas G in the injectable liquid from flowing into the outlet tube 22. As described above, in a conventional filter device, gas in the injectable liquid is not entirely discharged through an air discharge hole after passing through a gas permeable filter, i.e., a hydrophobic filter, but partially introduced into the extension tube connected to a patient.

In order to solve this problem, in the filter device 100' according to the second embodiment of the present invention, the blocking member 30' is also installed in the upper filter housing 20 to block the outlet tube 22. Longitudinal passages 38a', 38b' and 38c' are formed at a center portion of the block member 30' so that the injectable liquid L is introduced into the outlet tube 22 through the passages and discharged therefrom (see FIGS. 10 and 11).

As shown in FIGS. 10 and 11, the blocking member 30' is located in the upper filter housing 20. The blocking member 30' includes a front end 32' contacting with the injectable liquid in the upper filter housing 20, an outlet tube coupling portion 34' coupled to the outlet tube 22, and a distal end 36' contacting with the extension tube connected to the outlet tube 22. In the filter device 100' according to the second embodiment of the present invention, the blocking member 30' is directly connected to the extension tube unlike the first embodiment. Therefore, in the filter device 100' according to the second embodiment of the present invention, the capillary tube 40 and the O-shaped ring 50 of the first embodiment may be excluded.

In the filter device 100' according to the second embodiment of the present invention, the front end 32' and the outlet tube coupling portion 34' of the blocking member 30' have a long cylindrical shape, and the inner diameter of the front end 32' is substantially identical to the inner diameter of the distal end 36'.

In addition, as shown in FIGS. 10 and 11, anti-escaping projections 220a and 220b are formed on the inner wall of the outlet tube 22. The outlet tube coupling portion 34' of the blocking member 30' is formed to have an outer diameter conforming to the inner diameter of the anti-escaping projections 220a and 220b, and the distal end 36' of the blocking member 30' is formed to have an outer diameter conforming to the inner diameter of the outlet tube 22. Therefore, it is possible to prevent the gas G in the injectable liquid from flowing into the outlet tube 22 through the outlet hole 220c and ultimately to effectively prevent the gas G from flowing into the extension tube.

However, the present invention is not limited thereto, and various types of block members may be used in the present invention, including the aforementioned blocking member 30 of the first embodiment. Meanwhile, in the filter device 100' according to the second embodiment of the present invention, the blocking member 30' has a function identical to that of the filter device 100 according to the first embodiment, and therefore, the details thereof will be omitted.

Meanwhile, in the filter device 100' according to the second embodiment of the present invention, the blocking member 30' is preferably made of a silicone or plastic material, more preferably a silicone material.

Although preferred embodiments of the present invention have been described, the present invention is not limited thereto. It will be apparent that those skilled in the art can make various modifications and changes thereto without departing from the spirit and scope of the present invention and the modifications and changes are also included in the scope of the present invention.

I claim:

1. A filter device connected to a liquid supply line to filter and discharge an introduced liquid, the filter device comprising:
   an inflow tube having an inflow hole communicating with the liquid supply line and allowing a liquid introduced through the inflow hole to flow into an internal space of the filter device;
   a filter housing communicating with the inflow tube and communicating with the outside;
   an outlet tube having an outlet hole communicating with the filter housing, the outlet tube being disposed at a location opposite to the inflow tube, the outlet tube being spaced apart from the inflow tube substantially in parallel therewith to define a vertical space in the filter housing, the outlet tube allowing the liquid discharged from the filter housing to be transported to the outside;
   a hydrophilic filter located between the inflow tube and the vertical space in the filter housing, the hydrophilic filter filtering off solid impurities in the liquid introduced through the inflow hole;
   at least one hydrophobic filter located corresponding to at least one gas discharge hole provided in the filter housing, the hydrophobic filter allowing gas in the introduced liquid to be discharged to the outside before and/or after the liquid passes through the hydrophilic filter; and
   a blocking member for preventing gas in the liquid passing through the hydrophilic filter from flowing into the outlet tube, the blocking member being installed in the filter housing to block the outlet tube, the blocking member having a longitudinal passage formed in a center portion thereof so that the liquid is introduced into the outlet tube through the passage and discharged therefrom.

2. The filter device according to claim 1, wherein the filter housing includes an upper filter housing and a lower filter housing, which are detachably coupled.

3. The filter device according to claim 2, wherein the upper filter housing is connected to the outlet tube, and the lower filter housing is connected to the inflow tube.

4. The filter device according to claim 2, wherein a ring-shaped protrusion protruding upward or a ring-shaped concave portion is formed in an upper surface of the lower filter housing, and a ring-shaped concave portion or a ring-shaped protrusion protruding downward is correspondingly formed in a lower surface of the upper filter housing, so that the filter housing is coupled by fitting the protrusion or concave portion of the lower filter housing to the corresponding concave portion or protrusion of the upper filter housing.

5. The filter device according to claim 4, wherein the hydrophilic filter is located and fixed between an inner surface of the protrusion or concave portion of the lower filter housing and an inner surface of the concave portion or protrusion of the upper filter housing.

6. The filter device according to claim 2, wherein at least one gas discharge hole is formed in at least one of the upper filter housing and the lower filter housing, and a gas discharge portion is provided in an inner or outer portion of the filter housing having the gas discharge hole formed therein, the gas discharge portion including the hydrophobic filter corresponding to the gas discharge hole and a fixing means for fixing the hydrophobic filter to the inner or outer portion of the filter housing and having a hole for discharging the gas to the outside.

7. The filter device according to claim 6, wherein a filter seating portion protruding in a ring shape is formed in the outer portion of the filter housing having the gas discharge hole formed therein, the hydrophobic filter is seated on the filter seating portion, a ring-shaped groove is formed around the filter seating portion, and a protrusion with a shape conforming to the ring-shaped groove is formed on the fixing means of the gas discharge portion so that the hydrophobic filter is fixed without escape.

8. The filter device according to claim 6, wherein a depressed filter seating portion is formed in the inner portion of the filter housing having the air discharge hole formed therein, the hydrophobic filter is seated on the filter seating portion, a stepped insert portion is formed around the filter seating portion, and the fixing means of the gas discharge portion is stepwise formed corresponding to the stepped insert portion so that the hydrophobic filter is fixed without escape.

9. The filter device according to claim 1, wherein the blocking member includes a front end contacting with the liquid in the filter housing, an outlet tube coupling portion coupled to the outlet tube, and a distal end contacting with an extension tube connected to the outlet tube.

10. The filter device according to claim 9, wherein the front end has a tapered shape the size of which gradually decreases toward the inside of the filter housing, and an inner diameter of the front end is smaller than that of the distal end.

11. The filter device according to claim 9, wherein an inner wall of the outlet tube is formed with an anti-escaping projection, and the outlet tube coupling portion of the blocking member is formed with a ring-shaped groove, so that the groove of the outlet tube coupling portion of the blocking member is coupled to the anti-escaping projection of the outlet tube in a catching manner.

12. The filter device according to claim 9, wherein an anti-escaping projection is formed on an inner wall of the outlet tube, the outlet tube coupling portion of the blocking member is formed to have an outer diameter conforming to an inner diameter of the anti-escaping projection, and the distal end of the blocking member is formed to have an outer diameter conforming to an inner diameter of the outlet tube.

13. The filter device according to claim 9, wherein the distal end of the blocking member is in direct contact with the extension tube connected to the outlet tube or in close surface contact with a capillary tube installed in the extension tube.

14. The filter device according to claim 13, wherein the capillary tube is fixedly supported in the extension tube, a projection through which the liquid from the capillary tube can pass is installed in the extension tube, and the capillary tube is inserted into an O-shaped ring and is in close contact with and fixed to a coupling portion between the outlet tube and the extension tube.

15. The filter device according to claim 9, wherein the longitudinal passage of the blocking member has a tapered shape in which an inner diameter of the longitudinal passage gradually increases from the inside of the filter housing toward the outlet tube.

16. The filter device according to claim 15, wherein the longitudinal passage at the front end of the blocking member has an inner diameter of 0.4 mm, and the longitudinal passage at the distal end of the blocking member has an inner diameter of 0.8 mm.

17. The filter device according to claim 9, wherein the front end of the blocking member is located to protrude into the filter housing.

18. A liquid injection apparatus having the filter device defined in claim 1.

* * * * *